(12) United States Patent
Eder et al.

(10) Patent No.: US 6,596,694 B2
(45) Date of Patent: Jul. 22, 2003

(54) CALOPOROSIDE DERIVATIVES, METHODS OF THEIR PREPARATION AND USE

(75) Inventors: Claudia Eder, Hofheim (DE); Michael Kurz, Hofheim (DE); Mark Brönstrup, Frankfurt (DE); Luigi Toti, Hochheim (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 10/092,538

(22) Filed: Mar. 8, 2002

(65) Prior Publication Data

US 2002/0193316 A1 Dec. 19, 2002

(30) Foreign Application Priority Data

Mar. 9, 2001 (DE) .......................... 101 11 682

(51) Int. Cl.$^7$ ................................ A61K 31/70
(52) U.S. Cl. .................. 514/25; 514/23; 536/108; 536/103; 536/4.1
(58) Field of Search ...................... 514/23, 25; 536/4.1, 536/108, 103

(56) References Cited

PUBLICATIONS

Crich et al., tetrahedron Letters 39 (1998), 9339–9342.*
Crich et al., Convergent, Stereoselective Synthesis of the Caloporoside Disaccharide, *Tetrahedron Letters*, 39: 9339–9342, 1998.
Faenza, et al., A Role for Nuclear Phospholipase C$\beta_1$ in Cell Cycle Control, *The Journal of Biological Chemistry*, 275: 30520–30524, 2000.
Hajdúch et al., Synthetic Cyclin Dependent Kinase Inhibitors, in Drug Resistance in Leukemia and Lymphoma III (Kaspers et al., Eds.) Kluwer Academic/Plenum Publishers, New York, 1999, pp 341–53.
Ortega et al., Cyclin D–Dependent Kinases, INK4 inhibitors and Cancer, *Biochimica et Biophysica Acta*, 1602: 73–87, 2002.
Weber et al., Caloporoside, A New Inhibitor of Phospholipases C, *The Journal of Antibiotics*, 47: 1188–1194, 1994.
Remington's Pharmaceutical Sciences, p. 1418, 1985.
Shan et al., The Isolation of Two New Fungal Inhibitors of $^{35}$S–TBPS Binding to the Brain GABA$_A$/Bensodiazepine Chloride Channel Receptor Complex, *Nat. Prod. Lett.*, 4: 171–178, 1994.
Tatsuta et al., Total Synthesis of Deacetyl–caloporoside, A Novel Inhibitor of The GABA$_A$ Receptor Ion Channel, *Tetra. Lett.*, 37: 2453–2456, 1996.
The Merck Index, 12 Ed., Chemical No. 463.
The Merck Index, 12 Ed., Chemical No. 479.
The Merck Index, 12 Ed., Chemical No. 581–582.
The Merck Index, 12 Ed., Chemical No. 1025.
The Merck Index, 12 Ed., Chemical No. 1704.
Weber et al., Caloporoside, A New Inhibitor of Phospholipases C, *J. Antibiotics*, 47: 1188–1194, 1994.
Shan, et al., "The Isolation of two New Fungal Inhibotors of $^{35}$S–TBPS Binding to the Brain GABA$_A$/Benzodiazepine Chloride Receptor Complex," *Natural Product Letters*, 4: 171–178 (1994).
Weber, et al., "Caloporoside, A New Inhibotor of Phospholipases C From *Calopororus dichrous* (Fr.) Ryv.," *The Journal of Antibiotics*, 47(11): 1188–1194 (1994).

* cited by examiner

*Primary Examiner*—Samuel Barts
*Assistant Examiner*—Michael C. Henry
(74) *Attorney, Agent, or Firm*—Finnegan, Henderson, Farabow, Garrett and Dunner, L.L.P.

(57) ABSTRACT

The present invention relates to novel caloporoside derivatives and method of their use. The caloporoside derivatives may be formed by fermentation of microorganisms, such as *Gloeoporus dichrous* (Fr.: Fr.) Bres. ST001714 (DSM 13784). The invention also relates to use to a process for preparing caloporoside derivatives, drugs comprising such compounds, and methods of their use. The invention further relates to the microorganism *Gloeoporus dichrous* Bres. ST001714 (DSM 13784).

17 Claims, No Drawings

CALOPOROSIDE DERIVATIVES, METHODS OF THEIR PREPARATION AND USE

The present invention relates to novel caloporoside derivatives. The caloporoside derivatives may be formed by fermentation of microorganisms, such as *Gloeoporus dichrous* Bres. ST001714 (DSM 13784). The invention also relates to a process for preparing caloporoside derivatives, drugs comprising such compounds, and methods of their use. The invention further relates to the microorganism *Gloeoporus dichrous* Bres. ST001714 (DSM 13784).

Caloporoside was described for the first time in 1994 as a phospholipase C inhibitor (W. Weber et al. (1994) *J. Antibiotics*, 47:1188–1194). In the same year, two similar secondary metabolites were isolated (R. Shan et al. (1994) *Nat. Prod. Lett.*, 4:171–178). The compounds of formula I, described below, possess a different structure from those described in the prior art.

Cancer is usually a fatal disease in humans and animals caused by uncontrolled growth of endogenous cells. Cancer refers to the formation of malignant growths or neoplasms (i.e., tumors or carcinomas), or the malignant degeneration or disturbed maturation of white blood cells (leukemia or cancers of other blood cells). Cancer cells are formed through transformation of endogenous cells. The malignancy of cancer cells is evident from the autonomy of growth, i.e., their ability to grow and infiltrate in an uninhibited manner that is not restrained by the normal growth pattern of the organ; and from tissue destruction. A reliable indication of malignancy is the transfer (metastasis) of the disease away from the original site of the tumor to other parts of the body through the blood or lymph systems. Cancer is one of the most frequent causes of death in humans, and consequently there is a great demand for methods and agents that heal, treat, or prevent the disease.

Aside from radical surgical removal of a tumor, therapy for malignant tumors includes radiological therapy with X-rays, α-, β- and γ-rays, immunotherapy, and chemotherapy. Immunotherapy can presently be used only in a restricted manner. Chemotherapy of tumors refers to the administration of cytotoxic compounds to treat tumors and tumor cells remaining after local surgical treatment or irradiation. These substances interfere with certain processes of cell division. Consequently, tissues having a high proportion of dividing cells, such as the rapidly growing tumor tissue, are more sensitive to the cytotoxic effects. Typical chemotherapeutic agents include alkylating compounds, such as cyclophosphamide (The Merck Index, 12th Ed. page 463); antimetabolites, such as methotrexate (The Merck Index, 12th Ed. page 1025); alkaloids, such as vincristine (The Merck Index, 12th Ed. page 1704); and antibiotics, such as daunomycin (The Merck Index, 12th Ed. page 479) and adriamycin (The Merck Index, 12th Ed. page 581–582). However, all of these agents have major disadvantages owing to severe side effects, limiting their effective therapeutic use. Thus, the death of the patient may be delayed, but not prevented. In addition, the cancer cells develop resistance to such agents. When this occurs, the drugs no longer exhibit the intended therapeutic effect, but still cause toxic side effects. In addition, since combined or sequential use of cytotoxics exceeds the efficacy of a single cytotoxic (monotherapy), it also possible that the toxic side effects will be more than additive in their effects. For all these reasons, novel chemotherapeutic agents are urgently needed and are therefore being sought worldwide.

Cyclin-dependent kinases (CDKs) play a central role in regulating the cell cycle. They catalyze phosphorylation reactions, setting in motion a signaling cascade which initiates a transition from the G1 phase (growth phase 1) into the S phase (synthesis phase) of the cell cycle. Cyclin-dependent kinases therefore represent a promising therapeutic target for the treatment of cancer and other diseases affected by a pathological disturbance of cell proliferation. Low-molecular-weight inhibitors, which regulate the cell cycle and prevent uncontrolled cell division, would be useful as drugs to treat cancer patients.

Surprisingly, it has been found that the microorganism strain *Gloeoporus dichrous* (Fr.: Fr.) Bres. ST 001714 (DSM 13784) is capable of forming highly active novel cytotoxics which inhibit cyclin-dependent kinases at very low concentrations.

The invention accordingly relates to caloporoside derivatives, such as those formed by the *Gloeoporus dichrous* strain (Fr.: Fr.) Bres. ST 001714, DSM 13784, and the physiologically tolerated salts, esters and other chemical equivalents thereof.

The invention thus relates to compounds of the general formula I

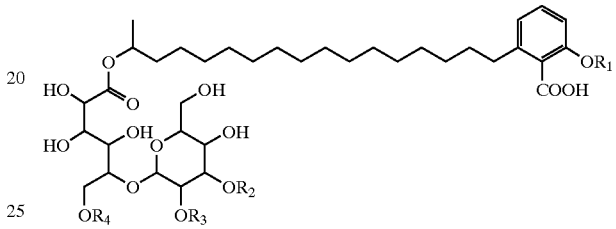

in which $R_1$, $R_2$ and $R_3$, independently of one another, are H or an acyl radical having 2–10 carbon atoms, 2 to 6 atoms, or 2 atoms; and $R_4$ is H or —C(O)(CH$_2$)$_n$COOH, in which n is from 1 to 7, 1 to 3, or 1 or 2;

with the exception that $R_1$, $R_2$, $R_3$ and $R_4$ are not all H; and physiologically tolerated salts thereof.

The acyl radicals in the compounds of formula I may be straight-chain or branched, saturated or mono- or diunsaturated.

An example of an acyl radical having 2 carbon atoms is an acetyl radical.

Examples of saturated, unbranched acyl radicals include an acetyl radical (C=2), propionyl radical (C=3), butyryl radical (C=4), valeryl radical (C=5), capronyl radical (C=6), oenanthyl radical (C=7), caproyl radical (C=8), perlagonyl radical (C=9) and capryl radical (C=10).

Examples of monounsaturated, unbranched acyl radicals include an acryloyl radical (C=3), crotonoyl radical (C=4), and a vinylacetyl radical (C=4).

An example of a diunsaturated, unbranched acyl radical is a sorbyl radical (C=6).

Caloporosides are weak antibiotics which consist of a salicylic acid and a disaccharide. The two structural units are linked via an alkyl chain. The sugar moiety of the compound of formula I may be a disaccharide consisting of a D-pyranose of an aldohexose (e.g., D-glucopyranose or D-galactopyranose) and the aldonic acid of an aldohexose (e.g., D-gluconic acid). For example, the sugar moiety may be D-mannopyranosyl-D-mannonic acid, which is unsubstituted or substituted by $R_2$, $R_3$ and/or $R_4$ as defined above.

The invention furthermore relates to a) a compound of formula I in which $R_1$ is acetyl; and $R_2$, $R_3$, and $R_4$ are H (=caloporoside B: empirical formula: $C_{38}H_{62}O_{16}$, MW 774.9) and physiologically tolerated salts thereof;

b) a compound of formula I in which $R_1$ and $R_3$ are acetyl; $R_2$ is H; and $R_4$ is malonyl (=caloporoside C: empirical formula: $C_{43}H_{66}O_{20}$, MW 902.99) and physiologically tolerated salts thereof;

c) a compound of formula I in which $R_1$ and $R_2$ are H; $R_3$ is acetyl; and $R_4$ is malonyl (=caloporoside D: empirical formula: $C_{41}H_{64}O_{19}$, MW 860.96) and physiologically tolerated salts thereof;

d) a compound of formula I in which $R_1$ and $R_3$ are H; $R_2$ is acetyl; and $R_4$ is malonyl (=caloporoside E: empirical formula: $C_{41}H_{64}O_{19}$, MW 860.96) and physiologically tolerated salts thereof;

e) a compound of formula I in which $R_1$, $R_2$, and R4 are H; and $R_3$ is acetyl (=caloporoside F: empirical formula: $C_{38}H_{62}O_{16}$, MW 774.9) and physiologically tolerated salts thereof.

Centers of chirality in the compounds of formula I, unless stated otherwise, may be in the R or the S configuration. The invention relates to both optically pure compounds and stereoisomeric mixtures, such as enantiomeric mixtures and diastereomeric mixtures.

The compounds of formula I can be obtained in accordance with the invention by fermentation of microorganisms, such as Gloeoporus dichrous (Fr.:Fr.) Bres. ST001714, DSM 13784, or of one of its variants or mutants, under suitable conditions in a culture medium until one or more of the caloporoside derivatives of formula I accumulates in the culture medium. The caloporoside derivatives are obtained by subsequent isolation of the compounds and, if desired, conversion into chemical equivalents and physiologically tolerated salts thereof.

The invention further relates to a process for preparing a compound of formula I, which comprises fermenting the microorganism Gloeoporus dichrous (Fr.:Fr.) Bres. ST001714 (DSM 13784) or one of its variants or mutants, under suitable conditions in a culture medium until one or more of the compounds of formula I accumulates in the culture medium; the compounds may be subsequently isolated and, if desired, converted into chemical equivalents and/or physiologically tolerated salts.

The strain ST001714 (DSM 13784), and mutants and/or variants thereof, are typically fermented in a nutrient solution or a solid medium (also known as culture medium) with a carbon and nitrogen source, and the usual inorganic salts, until the compounds according to the invention accumulate in the culture medium. The compounds are subsequently isolated from the culture medium and, where appropriate, separated into the individual active components.

The process according to the invention can be employed for fermentation on a laboratory scale (milliliter to liter range) and on an industrial scale (cubic meter scale).

The strain Gloeoporus dichrous (Fr.:Fr.) Bres. ST 001714 was cultivated in a preculture. An isolate was deposited at Deutsche Sammlung von Mikroorganismen und Zellkulturen GmbH, Mascheroder Weg 1B, 3300 Brunswick, Germany, under the terms of the Budapest Treaty on Dec. 14, 1999, under the number DSM 13784.

Gloeoporus dichrous (Fr.:Fr.) Bres. ST001714 (DSM 13784) has a white mycelle and crimson spores. It typically occurs in Betula, but can also infest other hosts, such as Alnus, Salix, Populus, Ulmus and Prunus.

It is also possible to employ mutants and variants of Gloeoporus dichrous (Fr.:Fr.) Bres. ST001714 (DSM 13784) which synthesize one or more of the presently disclosed compounds. Such mutants can be produced in a manner known in the art, for example, by physical means such as irradiation (e.g., ultraviolet or X-rays); or chemical mutagens, such asethyl methanesulfonate (EMS), 2-hydroxy-4-methoxybenzo phenone (MOB), or N-methyl-N'-nitro-N-nitrosoguanidine (MNNG).

The screening for mutants and variations which synthesize one or more of the compounds according to the invention is carried out in accordance with the following scheme:

lyophilization of the plate cultures;
extraction of the lyophilizate with an organic solvent;
extraction of the compound from the culture filtrate using solid phases;
analysis by HPLC, TLC or by testing the biological activity.

The fermentation conditions described below are generally useful for fermenting microorganisms, such as Gloeoporus dichrous (Fr.:Fr.) Bres. ST001714, (DSM 13784), and mutants and variants thereof.

In a nutrient solution containing a carbon source and a nitrogen source and the usual inorganic salts, Gloeoporus dichrous (Fr.:Fr.) Bres. ST001714 (DSM 13784) produces the presently disclosed caloporoside derivatives.

Suitable carbon sources for the fermentation include assimilatable carbohydrates and sugar alcohols, such as glucose, lactose, sucrose or D-mannitol; and carbohydrate-containing natural products, such as malt extract. Suitable nitrogen-containing nutrients include amino acids; peptides (including synthetic and biosynthetic peptides) and proteins and degradation products thereof, such as casein, peptones or tryptones; meat extracts; yeast extracts; ground seeds, such as those from corn, wheat, beans, soya or cotton plants; distillation residues from alcohol production; meat meals or yeast extracts; and ammonium salts and nitrates. Inorganic salts present in the nutrient solution may include, for example, chlorides, carbonates, sulfates or phosphates of the alkali or alkaline earth metals, iron, zinc, cobalt and manganese.

The formation of the compounds according to the invention proceeds, for example, in a nutrient solution which comprises from about 0.05 to 5%, optionally from 1 to 2% of malt extract; from 0.05 to 3%, optionally from 0.05 to 1% of yeast extract; from 0.2 to 5%, optionally from 0.5 to 2% of glucose; and from 0.5 to 3% of cellulose powder; and traces of ammonium sulfate. The data in percent are, in each case, based on the weight of the entire nutrient solution.

In this nutrient solution, Gloeoporus dichrous (Fr.:Fr.) Bres ST001714 (DSM 13784) produces a mixture of caloporoside derivatives. Depending on the composition of the nutrient solution, the proportional amounts of the various caloporoside derivatives may vary. In addition, the synthesis of individual caloporoside derivatives can be controlled by altering the composition of the nutrient solution, such that a caloporoside derivative is not produced at all by the microorganism or only in an amount below the detection limit.

The microorganism is typically cultivated aerobically, for example, submersed with shaking or stirring in shaking flasks or fermenters, with introduction of air or oxygen as appropriate; or on solid medium. It can be carried out in a temperature range from about 18 to 35° C., optionally at from about 20 to 30° C., or from 25 to 30° C. The pH range should be between 5 and 8, optionally between 5.5 and 6.5. The microorganism is generally cultivated under these conditions over a period of from 24 to 720 hours, optionally from 288 to 576 hours.

The cultivation is advantageously carried out in a number of steps. First, a mycelle is obtained, for example, by allowing a strain to grow for about 3 to 40 days, optionally from 10 to 30 days, on a solid or liquid nutrient medium such as malt-yeast-agar or potato-dextrose-agar. Second, a preculture is obtained, for example, by inoculating the mycelle into a nutrient solution and allowing it to grow for about 36 to 120 hours, optionally from 48 to 72 hours. Finally, one or more precultures in the liquid nutrient medium are inoculated into the actual production medium, the main culture, at a particular volume ratio, such as 1:10.

The course of the fermentation can be monitored from the pH of the cultures; the mycelle volume; by chromatographic methods, such as high-performance liquid chromatography (HPLC); or by testing the biological activity present in the culture medium.

The presently disclosed caloporoside derivatives may be isolated or purified as described below.

The isolation or purification of a caloporoside derivative according to the invention from the culture medium is carried out by known methods, taking into account the chemical, physical and biological properties of the natural products. HPLC may be used to test the concentration of the respective caloporoside derivatives in the culture medium or in the individual isolation steps by comparing the amount of the compounds formed with a calibration solution.

In order to isolate the compounds according to the invention, the culture in the nutrient solution or solid medium is lyophilized. The caloporoside derivatives are subsequently extracted from the lyophilisate with an organic solvent, which is optionally water-miscible. The organic solvent phase contains the caloporoside derivatives, which may, if desired, be concentrated under reduced pressure and purified further.

The further purification of one or more compounds according to the invention is carried out by chromatography on suitable materials, for example, on molecular sieves, silica gel, aluminum oxide, ion exchangers, absorber resins, or reversed phases (RPs). The caloporoside derivatives are separated with the aid of this chromatography. The chromatography of the caloporoside derivatives is carried out using buffered aqueous solutions or mixtures of aqueous and organic solutions.

Mixtures of aqueous or organic solutions are taken to mean all water-miscible organic solvents, such as methanol, propanol and acetonitrile, in a concentration of from 5 to 80% of solvent, optionally from 20 to 50% of solvent; or all buffered aqueous solutions which are miscible with organic solvents. The buffers to be used are the same as indicated below.

The separation of the caloporoside derivatives on the basis of their different polarity is carried out with the aid of reversed phase chromatography, for example, on MCI® (absorber resin from Mitsubishi, Japan) or Amberlite XAD® (TOSOHAAS); and hydrophobic materials, such as RP-8 or RP-18 phases. In addition, the separation can be carried out with the aid of normal phase chromatography, for example on silica gel, aluminum oxide or the like.

The chromatography of the caloporoside derivatives is carried out using buffered or acidified aqueous solutions or mixtures of aqueous solutions with alcohols or other water-miscible organic solvents. Suitable organic solvents include propanol or acetonitrile.

The term buffered or acidified aqueous solutions is taken to mean, for example, water, phosphate buffer, ammonium acetate, citrate buffer in a concentration of from 0 to 0.5 M, as well as formic acid, acetic acid, trifluoroacetic acid or any commercially available acids known to the person skilled in the art, typically in a concentration of from 0 to 1%. In the case of buffered aqueous solutions, 0.1% ammonium acetate may be used.

The chromatography is carried out with a gradient beginning with 100% water and ending with 100% solvent. For example, a linear gradient from 20 to 100% propanol or acetonitrile may be used.

Alternatively, it is possible to carry out gel chromatography or chromatography on hydrophobic phases.

Gel chromatography is carried out on polyacrylamide or copolymer gels such as Biogel-P 2® (Biorad) or Fractogel TSK HW 40® (Merck, Germany, or Toso Haas, USA).

The sequence of the above-mentioned chromatography methods is reversible.

The compounds according to the invention are stable in the solid state and in solutions in the pH range from 3 to 8, for example from 5 to 7, and can thus be incorporated into conventional pharmaceutical preparations.

One or more of the compounds according to the invention are suitable, owing to their valuable pharmacological properties, for use as drugs in human or veterinary medicine.

The present invention thus relates to the use of a compound of formula I or a physiologically tolerated salt thereof for the preparation of a cytotoxic pharmaceutical composition for the treatment of tumor diseases.

The present invention furthermore relates to all apparent chemical equivalents of the compounds of formula I. Such equivalents include compounds which have a slight chemical difference, i.e., have the same action or are converted into the compounds of formula I under mild conditions. The equivalents include, for example, salts, reduction products, esters, ethers, acetals or amides of the compounds of formula I; and equivalents which can be prepared by the person skilled in the art using standard methods. In addition, all optical antipodes, diastereomers and all stereoisomeric forms are included.

The term physiologically tolerated salts of compounds of formula I is taken to mean both the organic and inorganic salts thereof, as described In Remington's Pharmaceutical Sciences (17th Edition, page 1418 (1985)). Due to their physical and chemical stability and solubility, sodium, potassium, calcium and ammonium salts, inter alia, are suitable for acidic groups; salts of hydrochloric acid, sulfuric acid, phosphoric acid, carboxylic acids, or sulfonic acids, such as acetic acid, citric acid, benzoic acid, maleic acid, fumaric acid, tartaric acid and p-toluenesulfonic acid, inter alia, are suitable for basic groups.

Esters, ethers and acetals can be prepared by methods described in the literature, for example, in *Advanced Organic Synthesis*, $4^{th}$ Edition, J. March, John Wiley & Sons, 1992, or *Protective Groups in Organic Synthesis*, $3^{rd}$ Edition, T. W. Greene & P. G. M. Wuts, John Wiley & Sons, 1999.

The carboxyl group can be reduced to an alcohol, for example using $LiAlH_4$.

First, the glycoside moiety is cleaved off compounds of formula I by means of alkaline hydrolysis (W. Weber et al., *J. Antibiotics*, 47:1188–1194). Any desired sugar radical can subsequently be introduced by glycosylation (for example, a Königs-Knorr reaction). Corresponding methods are described in the literature, for example in *Carbohydrate Chemistry*, J. F. Kennedy, Oxford University Press, 1988.

While a mechanism of action of the caloporoside derivatives is not yet clear, a significant effect has been shown.

In order to detect the inhibitors of cyclin-dependent kinases (CDKs), use is made of a test in which the phosphorylation rate by the cyclin-dependent kinases of a specific peptide substrate is measured. The cyclin-dependent kinases are activated when the kinase binds to its respective cyclin. A [γ-P]-phosphate is transferred from [γ-P]-ATP to the peptide substrate by the activated CDK. The test is carried out in 96-well microtiter plates. The radioactivity of the [γ-P]-phosphate on the substrate is measured.

$IC_{50}$ values for the caloporoside derivatives are shown in Table 1; this is the concentration which deactivates 50% of CDK-4.

| | |
|---|---|
| Caloporoside B | 1.5 μM |
| Caloporoside C | 3.1 μM |
| Caloporoside D | 1.8 μM |
| Caloporoside E | 1.8 μM |
| Caloporoside F | 1.5 μM |

The present invention furthermore relates to drugs comprising at least one compound according to the invention.

One or more caloporoside derivatives according to the invention can be administered with or without a solvent. Typically, the compounds are used in a mixture with suitable adjuvants or excipient material. The excipient material used in drugs can be any of the conventional and pharmacologically tolerated excipient materials and/or adjuvants.

The drugs according to the invention are generally administered orally or parenterally, but rectal administration is also possible. Suitable solid or liquid pharmaceutical preparation forms include, for example, granules, powders, tablets, coated tablets, (micro)capsules, suppositories, syrups, emulsions, suspensions, aerosols, drops or injectable solutions in ampoule form and preparations with protracted active ingredient release. In addition, excipients and additives and/or adjuvants, such as disintegrants, binders, coating agents, swelling agents, glidants, lubricants, flavors, sweeteners or solubilizers may be used. Frequently used excipients or adjuvants include, for example, magnesium carbonate, titanium dioxide, lactose, mannitol and other sugars, talc, milk protein, gelatine, starch, vitamins, cellulose and derivatives thereof, animal or vegetable oils, polyethylene glycols and solvents such as sterile water, alcohols, glycerol and polyhydric alcohols.

If desired, the dosage units for oral administration can be microencapsulated in order to delay release or extend release over a longer period, for example, by coating or embedding the active ingredient in particle form in suitable polymers, waxes or the like.

The pharmaceutical preparations are typically prepared and administered in dosage units, with each unit containing, as active constituent, a certain dose of one or more of the presently disclosed caloporoside derivatives. In the case of solid dosage units, such as tablets, capsules and suppositories, this dose can be up to about 500 mg, optionally from about 0.1 to 200 mg; and in the case of injection solutions, such as ampoule form, the dose can be up to about 200 mg, optionally from about 0.5 to 100 mg, per day.

The daily dose to be administered is dependent on the body weight, age, sex and health of the mammal. Under certain circumstances, however, higher or lower daily doses may also be administered. The daily dose can be administered either by a single administration in the form of a single dosage unit, or in a number of smaller dosage units, and by multiple administration of divided doses at certain intervals.

The drugs according to the invention are prepared by converting one or more of the compounds according to the invention into a suitable administration form with conventional excipients and optional additives and/or adjuvants.

The invention is explained in greater detail in the following examples. Percentages relate to the weight. Mixing ratios in the case of liquids relate to the volume, unless otherwise stated.

EXAMPLES

Example 1

Preparation of a Glycerol Culture of *Gloeoporus dichrous* (Fr.:Fr.) Bres. ST001714 (DSM 13784)

100 ml of nutrient solution (malt extract 2.0%, yeast extract 0.2%, glucose 1.0%, $(NH_4)_2 HPO_4$ 0.05%, pH 6.0) in a sterile 300 ml conical flask were incubated for 7 days at 25° C. and 140 rpm on a rotating shaking machine with the strain *Gloeoporus dichrous* (Fr.:Fr.) Bres. ST001714, DSM 13784. 1.5 ml of this culture were subsequently diluted with 2.5 ml of 80% glycerol and stored at −135° C.

Example 2

Preparation of a Preculture of *Gloeoporus dichrous* (Fr.:Fr.) Bres. ST001714 (DSM 13784)

30 ml of nutrient solution (malt extract 2.0%, yeast extract 0.2%, glucose 1.0%, $(NH_4)_2 HPO_4$ 0.05%, pH 6.0) in a sterile 100 ml conical flask were inoculated with the strain *Gloeoporus dichrous* (Fr.:Fr.) Bres. ST001714, DSM 13784, and incubated for 4 days at 25° C. and 140 rpm in a rotating shaking machine. The plates were each subsequently inoculated with 2 ml of this preculture during preparation of the main cultures.

Example 3

Preparation of a Main Culture of *Gloeoporus dichrous* (Fr.:Fr.) Bres. ST001714 (DSM 13784)

200 ml of the following nutrient solution were poured into sterile 25×25 cm plates (Nunc): 20 g/l of malt extract, 2 g/l of yeast extract, 10 g/l of glucose and 0.5 g/l of $(NH_4)_2 HPO_4$ pH 6.0. These plates were each inoculated with 2 ml of a preculture. The maximum production of one or more of the compounds according to the invention was achieved after about 480 hours.

Example 4

Preparation of the Caloporoside Derivatives 50 plates measuring 25×25 cm were produced and inoculated with the preculture:

nutrient medium:
  20 g/l of malt extract
  2 g/l of yeast extract
  10 g/l of glucose
  0.5 g/l of $(NH_4)_2HPO_4$
  pH 6 (before sterilization)

The plates were incubated for 480 hours at a temperature of 25° C.

Example 5

Isolation of the Caloporoside Mixture from the Plate Cultures of *Gloeoporus dichrous (Fr.:Fr.)* Bres. *ST*001714 (DSM 13784)

After completion of the fermentation of *Gloeoporus dichrous* (Fr.: Fr.) Bres. ST001714, DSM 13784, the plate cultures obtained in accordance with Example 3 or 4 were lyophilized, and the lyophilizate was extracted with 5 liters of methanol. The methanolic solution containing the target compounds was separated from cellular residue by filtration, and concentrated under reduced pressure. The concentrate was diluted with water and applied to a prepared 1.0 liter MCI GEL, CHP20P column. The elution was carried out with a gradient from water to 100% acetonitrile. The column eluate (25 ml per minute) was collected in fractions (25 ml each), and the fractions containing caloporoside derivatives (from 40% to 100% acetonitrile) were combined.

Concentration under reduced pressure and subsequent lyophilization yielded 8.5 g of a yellow-brown powder.

Example 6

Pre-separation of the Caloporoside Derivatives by RP18 Chromatography 0.5 g of the product obtained in accordance with Example 5 were applied to a Nucleosil® 100-7 C18 HD column (size: 40 mm×250 mm). The elution was carried out with a gradient from 20% acetonitrile (+water with addition of 0.1% of ammonium acetate) to 100% acetonitrile at a flow rate of 35 ml per minute. The column outflow was collected in fractions (35 ml). The caloporoside derivatives were present principally in fractions 39 to 68. These fractions were combined, freed from solvent under reduced pressure, and subsequently lyophilized, yielding caloporoside B (22.4 mg) and F (10.5 mg) in a purity of >95%. Caloporoside C (fraction 41; 43.4 mg), D (fractions 43–45; 76.2 mg) and E (fractions 43–45; 76.2 mg) were obtained in a purity of about 70% and were therefore further purified by chromatography.

Example 7

Purification of Caloporosides C, D and E 20 mg of caloporoside C isolated and concentrated in accordance with Example 6 were applied to a LUNA® 5μ C18(2) column (size: 10 mm×250 mm) and chromatographed with a gradient from 25 to 35% acetonitrile in 0.1% ammonium acetate/water. The flow rate of the eluent through the column was 6.5 ml per minute, and the fraction size is 6.5 ml. Caloporoside C was located in fractions 35 to 42. Lyophilization of the fractions yielded caloporoside C in a purity of >95% (7.6 mg). 25 mg of the mixture of caloporosides D and E, isolated and concentrated in accordance with Example 6, were applied to a LUNA® 5μ C18(2) column (size: 10 mm×250 mm) and chromatographed with a gradient from 30 to 40% acetonitrile in 0.1% ammonium acetate/water. The flow rate of the eluent through the column was 6.5 ml per minute, and the fraction size was 6.5 ml. Caloporoside D was located in fractions 18 to 19, and caloporoside E was located in fractions 20 to 21. Lyophilization of these fractions yielded caloporoside D (7.0 mg) and caloporoside E (6.0 mg) in a purity of >95%.

The physical/chemical and spectroscopic properties of the substances according to the invention are summarized as follows.

Caloporoside B:
Empirical formula: $C_{38}H_{62}O_{16}$
Molecular weight: 774.9
UV maxima: 208, 244, 310
$^1$H- and $^{13}$C-NMR: see Table 2
The high-resolution FAB mass spectrum showed an intensive MH$^+$ at m/e 775.4120 Da, in good agreement with the calculated weight (for $C_{38}H_{63}O_{16}$, monoisotopic) of 775.4116 Da.

Caloporoside C:
Empirical formula: $C_{43}H_{66}O_{20}$
Molecular weight: 902.99
UV maxima: 208, 244, 310
$^1$H- and $^{13}$C-NMR: see Table 3
The high-resolution FAB mass spectrum showed an intensive M+H$^+$ at m/e 903.4264 Da, in good agreement with the calculated weight (for $C_{36}H_{71}O_{25}$, monoisotopic) of 903.4284 Da.

Caloporoside D:
Empirical formula: $C_{41}H_{64}O_{19}$
Molecular weight: 860.96
UV maxima: 208, 244, 310
$^1$H- and $^{13}$C-NMR: see Table 4
The high-resolution FAB mass spectrum showed an intensive M+Na$^+$ at m/e 883.3942 Da, in good agreement with the calculated weight (for $C_{41}H_{64}O_{19}Na$, monoisotopic) of 883.3939 Da.

Caloporoside E:
Empirical formula: $C_{41}H_{64}O_{19}$
Molecular weight: 860.96
UV maxima: 208, 244, 310
$^1$H- and $^{13}$C-NMR: see Table 4
The high-resolution FAB mass spectrum showed an intensive M+Na$^+$ at m/e 883.3942 Da, in good agreement with the calculated weight (for $C_{41}H_{64}O_{19}Na$, monoisotopic) of 883.3939 Da.

Caloporoside F:
Empirical formula: $C_{38}H_{62}O_{16}$
Molecular weight: 774.9
UV maxima: 208, 244, 310
$^1$H- and $^{13}$C-NMR: see Table 5
The high-resolution FAB mass spectrum showed an intensive M+H$^+$ at m/e 775.4128 Da, in good agreement with the calculated weight (for $C_{38}H_{63}O_{16}$, monoisotopic) of 775.4116 Da.

TABLE 2

$^1$H and $^{13}$C chemical shifts of caloporoside B in methanol-$d_4$ and DMSO-$d_6$ at 300K

|  | DMSO | MeOD | DMSO | MeOD |
|---|---|---|---|---|
| 1 | — | — | 171.24 | a) |
| 2 | — | — | a) | a) |
| 3 | — | — | 162.22 | 163.57 |
| 4 | 6.68 | 6.77 | 115.28 | 116.81 |
| 5 | 7.17 | 7.25 | ~131.6 | b |
| 6 | 6.57 | 6.67 | 121.02 | ~123.0 |
| 7 | — | — | 137.90 | 139.57 |
| 8 | a) | a) | a) | a) |
| 9 | a) | a) | a) | a) |
| 10–20 | 1.30–1.20 | 1.32–1.27 | 29.01–28.69 | 30.76–30.47 |
| 21 | 1.30 | 1.38/1.32 | 24.81 | 26.52 |
| 22 | 1.54/1.45 | 1.65/1.52 | 35.31 | 37.00 |
| 23 | 4.81 | 4.95 | 70.04 | 73.09 |
| 24 | 1.15 | 1.24 | 19.69 | 20.22 |
| 1' | — | — | 173.43 | 175.35 |
| 2' | 3.95 | 4.13 | 70.89 | 72.97 |
| 3' | 3.95 | 4.17 | 70.04 | 71.59 |
| 4' | 3.54 | 3.82 | 67.96 | 69.80 |
| 5' | 3.65 | 3.86 | 78.94 | 80.12 |
| 6' | 3.74/3.44 | 3.90/3.69 | 62.11 | 63.25 |
| 1" | 4.53 | 4.71 | 100.27 | 101.34 |
| 2" | 3.74 | 3.95 | 70.37 | 72.46 |
| 3" | 3.22 | 3.44 | 73.67 | 75.30 |
| 4" | 3.21 | 3.49 | 67.54 | 69.00 |
| 5" | 3.04 | 3.22 | 77.15 | 78.23 |
| 6" | 3.72/3.31 | 3.88/3.63 | 61.80 | 63.25 |
| Ac—C' | — | a) | — | a) |
| Ac—Me | a) | a) | a) | a) | a)For these protons/carbon atoms, no signal is observed in MeOD or DMSO (aggregation).

TABLE 3

$^1$H and $^{13}$C chemical shifts of caloporoside C in methanol-$d_4$ at 300K

|  | $^1$H | $^{13}$C |
|---|---|---|
| 1 | — | 175.90 |
| 2 | — | 116.73 |
| 3 | — | 163.67 |
| 3-Ac—Me | a) | a) |
| 3-Ac—C' | — | a) |
| 4 | 6.73 | 116.73 |
| 5 | 7.16 | ~132.6 b) |
| 6 | 6.55 | 123.53 |
| 7 | — | 139.51 |
| 8 | 2.49 | 43.06 |
| 9 | 1.53 | 24.75 |
| 10–20 | 1.36–1.26 | 30.78–30.62 |
| 21 | 1.38/1.33 | 26.54 |
| 22 | 1.65/1.52 | 37.02 |
| 23 | 4.95 | 73.04 |
| 24 | 1.24 | 20.22 |
| 1' | — | 175.17 |
| 2' | 4.17 | 72.82 |
| 3' | 4.08 | 71.60 |
| 4' | 3.71 | 69.79 |
| 5' | 4.07 | 76.38 |
| 6' | 4.60/4.14 | 66.43 |
| 7' | — | 170.55 |
| 8' | 3.27 (c | ~44.8 |
| 9' | — | 173.12 |
| 1" | 4.93 | 99.40 |
| 2" | 5.33 | 73.40 |
| 3" | 3.72 | 73.40 |

TABLE 3-continued $^1$H and $^{13}$C chemical shifts of caloporoside C in methanol-d$_4$ at 300K

|  | $^1$H | $^{13}$C |
|---|---|---|
| 4" | 3.42 | 69.34 |
| 5" | 3.34 | 78.19 |
| 6" | 3.89/3.62 | 63.11 |
| 2"-Ac—Me | 2.11 | 21.17 |
| 2"-Ac—C' | — | 172.56 | a)No signal is observed for these nuclei (strong signal broadening).
b)Signal broadening.
c)The signal for the protons in position 8' is only observed in the freshly prepared solution (rapid exchange with deuterium).

TABLE 4

$^1$H and $^{13}$C chemical shifts of caloporosides D and E in methanol-d$_4$ at 300K

|  | $^1$H Caloporoside D | 13C Caloporoside D | $^1$H Caloporoside E | $^{13}$C Caloporoside E |
|---|---|---|---|---|
| 1 | — | — | 176.28 | 176.28 |
| 2 | — | — | 120.37 | 120.37 |
| 3 | — | — | 162.12 | 162.12 |
| 4 | 6.61 | 6.61 | 114.91 | 114.91 |
| 5 | 7.06 | 7.06 | 131.53 | 131.53 |
| 6 | 6.58 | 6.58 | 122.23 | 122.23 |
| 7 | — | — | 147.22 | 147.22 |
| 8 | 3.04 | 3.04 | 36.31 | 36.31 |
| 9 | 1.55 | 1.55 | 33.35 | 33.35 |
| 10–20 | 1.36–1.25 | 1.36–1.25 | 31.07–30.61 | 31.07–30.61 |
| 21 | 1.38/1.32 | 1.38/1.32 | 26.53 | 26.53 |
| 22 | 1.65/1.53 | 1.65/1.53 | 37.01 | 37.01 |
| 23 | 4.95 | 4.95 | 73.13a) | 73.07a) |
| 24 | 1.24 | 1.24 | 20.23 | 20.23 |
| 1' | — | — | 175.18 | 175.40 |
| 2' | 4.17 | 4.15 | 72.80 | 72.80 |
| 3' | 4.08 | 4.15 | 71.61 | 71.53 |
| 4' | 3.71 | 3.85 | 69.78 | 69.27 |
| 5' | 4.07 | 4.08 | 76.40 | 77.07 |
| 6' | 4.58/4.14 | 4.59/4.24 | 66.35 | 65.43 |
| 7' | — | — | ~170.4 | ~170.4 |
| 8' | 3.28 | 3.28 | ~45.0 | ~45.0 |
| 9' | — | — | ~173.0 | ~173.0 |
| 1" | 4.93 | 4.84 | 99.40 | 100.20 |
| 2" | 5.33 | 4.03 | 73.41 | 70.27 |
| 3" | 3.72 | 4.78 | 73.39 | 77.44 |
| 4" | 3.42 | 3.71 | 69.32 | 66.35 |
| 5" | 3.34 | 3.38 | 78.35 | 78.00 |
| 6" | 3.91/3.62 | 3.89/3.65 | 63.09 | 62.96 |
| 2"/3"-Ac—Me | 2.11 | 2.00 | 21.18 | 20.98 |
| 2"/3"-Ac—C' | — | — | 172.59 | 172.36 | a)These signals cannot be definitively assigned.

TABLE 5

$^1$H and $^{13}$C chemical shifts of caloporoside F in methanol-d$_4$ at 300K

|  | $^1$H | $^{13}$C |
|---|---|---|
| 1 | — | 174.95 |
| 2 | — | 117.32 |
| 3 | — | 162.18 |
| 4 | 6.68 | 115.42 |
| 5 | 7.17 | 133.17 |
| 6 | 6.67 | 122.65 |
| 7 | — | 146.91 |
| 8 | 2.93 | 36.57 |
| 9 | 1.56 | 33.27 |
| 10–20 | 1.36–1.25 | 30.93–30.62 |
| 21 | 1.35 | 26.53 |
| 22 | 1.65/1.53 | 37.02 |
| 23 | 4.95 | 73.05 |

TABLE 5-continued $^1$H and $^{13}$C chemical shifts of caloporoside F in methanol-d$_4$ at 300K

|  | $^1$H | $^{13}$C |
|---|---|---|
| 24 | 1.24 | 20.23 |
| 1' | — | 175.15 |
| 2' | 4.17 | 72.98 |
| 3' | 4.09 | 71.73 |
| 4' | 3.71 | 69.88 |
| 5' | 3.85 | 79.59 |
| 6' | 3.90/3.61 | 63.57 |
| 1" | 4.88 | 99.76 |
| 2" | 5.37 | 73.52 |
| 3" | 3.63 | 73.56 |
| 4" | 3.46 | 69.27 |
| 5" | 3.28 | 78.33 |
| 6" | 3.91/3.63 | 63.06 |
| Ac—C' | — | 173.03 |
| Ac—Me | 2.13 | 21.21 |

Example 8

Bioassay for CDK-4 Inhibitors

For the determination of the IC$_{50}$ value, stock solutions of the caloporoside derivatives according to the invention were prepared in a concentration of 10 mM. 384-well flash plates were coated with 50 μl (50 μg/well) of biotinylated peptide substrate at room temperature, incubated for 2 hours, and subsequently washed 3× with PBS buffer. For the reaction, 30 μl of a buffer-diluted solution of the caloporoside derivatives and 20 μl of a pre-mixed ATP/cyclin D1/CDK4 solution (final concentration: 1 μCi of 33P-γ-ATP, 2 μM of ATP and 1 μg of enzyme mixture) were pipetted onto the plates. After a reaction time of 2 hours at 37° C., the plates were washed 3× with 80 μl of 3% phosphoric acid. Radioactivity was subsequently measured for 30 seconds in a MicroBeta counter. The percentage inhibition was determined with the aid of mathematical equations. For the determination of IC$_{50}$ values, 10 different concentrations of the compounds according to the invention in a freshly diluted DMSO solution were tested.

We claim:

1. A compound of formula I

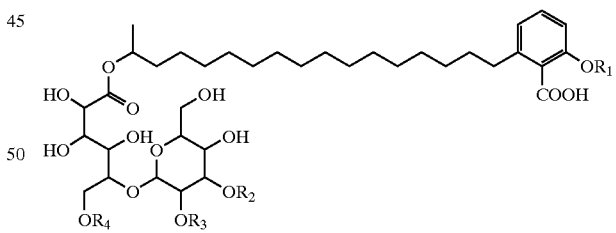

wherein:

R$_1$, R$_2$ and R$_3$, independently of one another, are H or acyl radicals having from 1 to 10 carbon atoms; and R$_4$ is H or —C(O)(CH$_2$)$_n$COOH, in which n is from 1 to 7;

with the exception that R$_1$, R$_2$, R$_3$ and R$_4$ are not all H; and physiologically tolerated salts thereof.

2. The compound of claim 1, wherein:

R$_1$, R$_2$ and R$_3$, independently of one another, are H or acetyl; and

R$_4$ is H or malonyl;

and physiologically tolerated salts thereof.

3. The compound of claim 1, wherein:
$R_1$ is acetyl; and
$R_2$, $R_3$ and $R_4$ are H;
and physiologically tolerated salts thereof.

4. The compound of claim 1, wherein:
$R_1$ and $R_3$ are acetyl;
$R_2$ is H; and
$R_4$ is malonyl;
and physiologically tolerated salts thereof.

5. The compound of claim 1, wherein:
$R_1$ and $R_2$ are H;
$R_3$ is acetyl; and
$R_4$ is malonyl;
and physiologically tolerated salts thereof.

6. The compound of claim 1, wherein:
$R_1$ and $R_3$ are H;
$R_2$ is acetyl; and
$R_4$ is malonyl;
and physiologically tolerated salts thereof.

7. The compound of claim 1, wherein:
$R_1$, $R_2$ and $R_4$ are H; and
$R_3$ is acetyl;
and physiologically tolerated salts thereof.

8. The compound of claim 1, prepared by the process of fermenting the microorganism *Gloeoporus dichrous* (Fr.:Fr.) Bres. ST001714 (DSM 13784), or one of its variants or mutants, under suitable conditions to produce one or more caloporoside derivatives, and isolating one or more of the caloporoside derivatives thus produced.

9. A process for preparing a compound of claim 1, comprising fermenting the microorganism *Gloeoporus dichrous* (Fr.:Fr.) Bres. ST001714 (DSM 13784), or one of its variants or mutants, under suitable conditions to produce one or more caloporoside derivatives.

10. The process of claim 9, wherein one or more of the caloporoside derivatives is isolated.

11. The process of claim 9, wherein one or more of the caloporoside derivatives is converted into a physiologically tolerated salt.

12. The process of claim 9, wherein the fermentation is carried out under aerobic conditions at a temperature of from 18 to 35° C. and a pH of from 5 to 8.

13. A pharmaceutical composition comprising one or more compounds of claim 1.

14. A method of inhibiting a cyclin dependent kinase (CDK) comprising contacting one or more CDKs with one or more compounds of claim 1.

15. A method of treating a cancer or other medical condition characterized by abnormal cell proliferation comprising administering one or more compounds of claim 1 to a patient in need of such a treatment.

16. The composition of claim 13, comprising a physiologically tolerated salt of a compound of formula I.

17. The composition of claim 13, wherein the composition comprises one or more pharmaceutically acceptable adjuvants or excipients.

* * * * *